United States Patent [19]

Furnish

[11] Patent Number: 5,489,290
[45] Date of Patent: Feb. 6, 1996

[54] FLUSH PORT FOR ENDOSCOPIC SURGICAL INSTRUMENTS

[75] Inventor: Greg Furnish, Lawrenceville, Ga.

[73] Assignee: Snowden-Pencer, Inc., Tucker, Ga.

[21] Appl. No.: 69,220

[22] Filed: May 28, 1993

[51] Int. Cl.$^6$ ............................................. A61B 17/32
[52] U.S. Cl. ...................... 606/170; 606/205; 128/751; 604/22
[58] Field of Search .................... 606/170, 171, 606/205, 206, 207, 208, 174; 604/22; 128/751, 752; 411/393, 395; 403/362

[56] References Cited

U.S. PATENT DOCUMENTS

| | | | |
|---|---|---|---|
| 2,295,314 | 9/1942 | Whitney | 411/393 |
| 3,618,611 | 11/1971 | Urban | 606/170 |
| 4,258,716 | 3/1981 | Sutherland | 606/170 |
| 4,848,338 | 7/1989 | De Satnick et al. | 606/171 X |
| 5,368,606 | 11/1994 | Marlow et al. | 606/170 |

OTHER PUBLICATIONS

Promotional Literature, Week Endoscopy, Sep. 1992.
Promotional Literature, Marlow Surgical Technologies, Inc., Sep. 1992.
Promotional Literature, Cabot Medical, Jan. 1993.
Promotional Literature, Jarit Roto–Lok™, (Date Unknown).

*Primary Examiner*—Michael H. Thaler
*Attorney, Agent, or Firm*—Needle & Rosenberg

[57] ABSTRACT

An endoscopic surgical instrument having a surgical tool with at least one articulated member, a handle, a hollow elongated shaft connecting the tool and handle and having a hole in the shaft for flushing the shaft, and an actuating rod slidably disposed within the lumen of the shaft connecting the handle and the articulated member such that the handle can also be used to actuate the articulated member. Specifically, an endoscopic surgical instrument and an apparatus for attaching to endoscopic surgical instruments having a removable flush port which is in fluid communication with the lumen of the shaft and a removable collar which is removably affixed on the shaft of the instrument by the flush port such that the flush port simultaneously functions as a flush port and as a means for affixing the collar on the shaft.

9 Claims, 1 Drawing Sheet

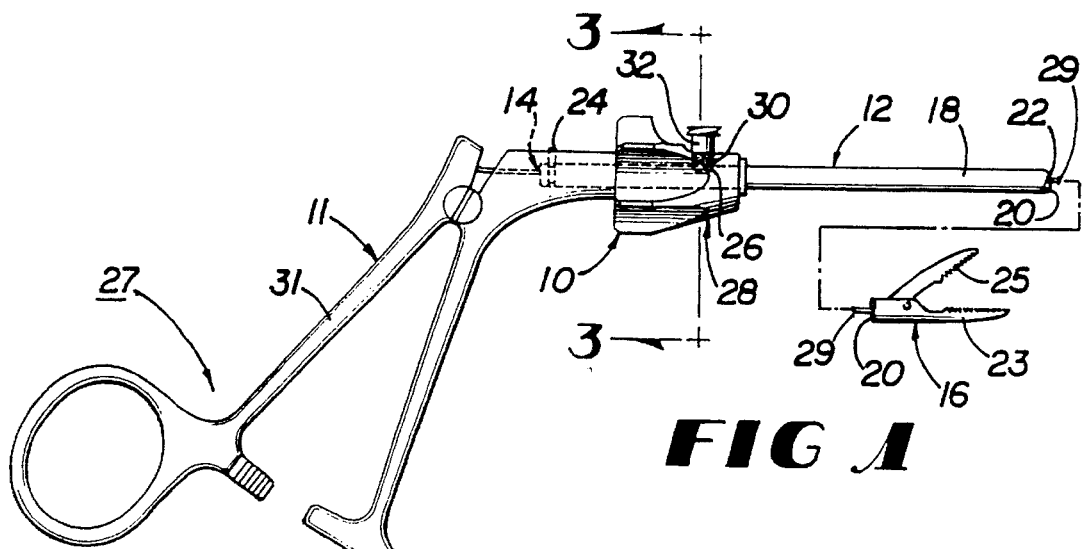
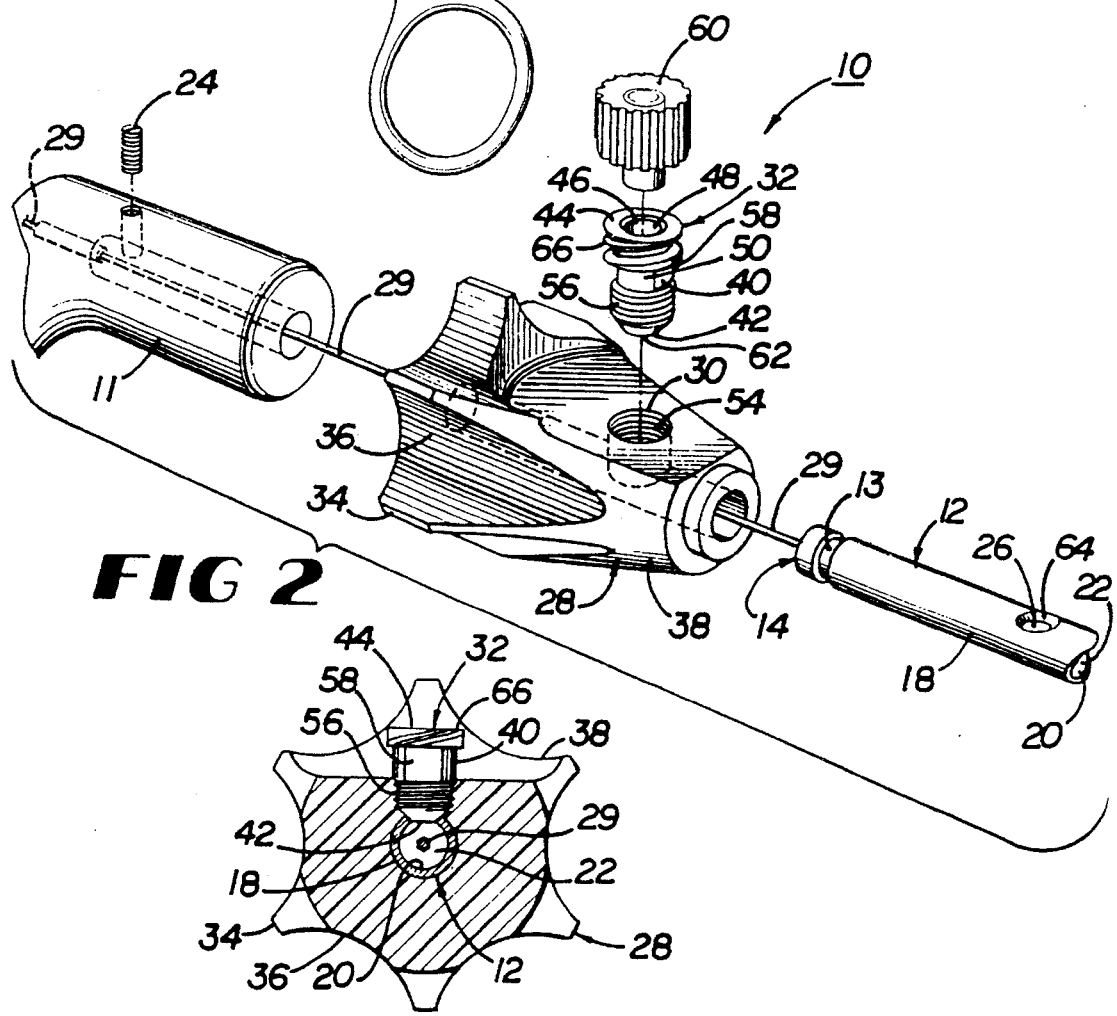

FLUSH PORT FOR ENDOSCOPIC SURGICAL INSTRUMENTS

BACKGROUND OF THE INVENTION

1. Field of the Invention

This invention relates to endoscopic surgical instruments having flush ports. More particularly, the invention relates to a surgical tool with at least one articulated member, a handle with actuating means for movement of the articulated member, a hollow elongated shaft connecting the tool and handle and having a hole in the shaft for flushing the shaft, and an actuating rod connecting the actuating means and articulated member such that the rod is slidably disposed within the lumen of the shaft. Specifically, the present invention relates to a means for affixing a removable collar to the shaft of the instrument whereby the affixing means can also function as a flush port for flushing the shaft via the hole in the shaft.

2. Background Art

Endoscopic surgical procedures are rapidly replacing conventional surgical techniques in a variety of applications. Diagnostic or therapeutic endoscopy procedures are generally preferred because they reduce trauma, decrease the risk of infection at incision sites, and increase patient recovery times. Arthroscopy procedures, for example, have all but replaced arthrotomy approaches for joint repair. Likewise, laparoscopic surgery is rapidly becoming the method of choice for a variety of abdominal procedures that once required large laparotomy incisions.

The laparoscope allows the surgeon to perform surgery within the abdomen by providing visualization of an internalized surgical field. The laparoscope and related instruments are usually introduced into the abdomen through a self-sealing cannula introduced into the abdomen via a small incision or trocharized opening in the abdominal wall. These small openings are generally sealed around the cannula during the procedure, thereby preventing airborne contamination of the surgical field and escape of insufflation gases. After surgery, the incision sites are easily closed and usually heal quickly with minimal scarring.

The growing popularity of laparoscopic surgery and the continuing development of new laparoscopic surgical techniques has created a need for specialized surgical instruments. As a result, many surgical instruments have been designed to meet the special needs of the laparoscopic surgeon. Most of these instruments, by necessity, contain certain basic design similarities. For example, in instruments which are comprised of a tool with an articulated member which must be actuated by means located on the handle, the handle is usually connected to the surgical tool via an elongated hollow shaft which contains an actuating rod connecting the tool and actuating means. This elongated shaft design allows the surgical tool to be introduced into the abdomen through the cannula while allowing the surgeon to operate the tool via the actuating means on the handle from a point external of the abdomen. Examples of such instruments include various retractors, hemostats, tissue clamps, needle holders, and the like.

A major problem with laparoscopic instruments having the hollow shaft design is that the lumen of the shaft acts as a reservoir for surgical debris and contaminants. Tissue fragments, blood and other body fluids can become trapped in the lumen and serve as a nidus for bacterial growth and a means for transferring disease from patient to patient.

As a result, instruments were developed with a proximally located flush port or tube on the shaft which allows for irrigation and flushing the lumen of the shaft to remove tissue debris and contaminants. The tubes currently in use are usually constructed of plastic or metal and are firmly attached to the shaft with a glue, weld, or other sealant, or they are molded into the shaft at manufacture. Therefore, these ports cannot be removed or replaced if damaged. Likewise, the surgeon is limited to attaching a flush source which has end connectors that are complimentary to those of the flush port.

A second design problem arose out of the surgeon's need to change the orientation of the tool with respect to the handle during surgery and resulted in instruments designed with rotatable shafts. In these instruments, a collar is permanently attached around the shaft acting as a knob for rotating the shaft about the long axis of the instrument. The collar of currently available instruments cannot be easily removed for cleaning or replaced with a collar of a different configuration.

Therefore, there still exists a need in the art for an instrument with a flush port or tube which is easily removable if damaged or to change the configuration of the tube connector by the surgeon if desired. There also exists a need for an instrument which has a collar which is easily removable for cleaning or for a change in configuration.

The present invention satisfies these needs by providing an instrument which has a removable flush port and a removable collar. Moreover, the present invention incorporates the means for removably affixing the collar to the shaft into the design of a removable flush port. The removable flush port, which simultaneously affixes the collar, saves time during instrument assembly and repair, allows for removal of the collar for thorough cleaning or repair, and allows the surgeon flexibility to change configuration of the collar or flush connector.

SUMMARY OF THE INVENTION

The present invention provides an apparatus to be affixed to an endoscopic surgical instrument of the type having a hollow elongate shaft having a proximal end, an opposite distal end, an external surface and a luminal surface defining a lumen. A surgical tool having at least one articulated member is connected to the distal end of the shaft. A handle, including actuating means is connected to the proximal end of the shaft for imparting motion to the articulated member. An actuating rod is slidably disposed within the lumen of the shaft that connects the actuating means to the surgical tool, the shaft further having a hole in the external surface in communication with the luminal surface. A removable collar for sliding on the shaft is provided with an opening therethrough which may be placed in registration with the hole in the shaft. An affixing device for attaching the collar to the shaft is provided that is receivable within and detachably removable from the opening in the collar and the hole in the shaft, such that the collar is thus held in place in the proper location to allow flushing of the lumen of the shaft through the collar assembly.

The collar can be attached to the shaft from either end of the shaft by sliding the collar over the external surface of the shaft to the appropriate location and adding the affixing means to secure the collar on the shaft. The collar can also be easily removed for cleaning, repair, or to change to a different collar configuration by reversing this process.

The removable affixing means may comprise a tube having a first end, an opposite second end, a luminal surface defining a lumen and an opposite external surface, wherein the lumen of the tube is in fluid communication with the lumen of the shaft such that the affixing means for the collar also functions as a means for flushing the lumen of the shaft. The collar may also provide a means for causing rotation of the shaft and surgical tool when they are rotatably connected to the handle such as raised ribs extending from the collar. Because the collar is removable, it can be removed for cleaning the instrument or interchanged for a collar of a different configuration thereby increasing the utility of the instrument.

In a preferred embodiment, the affixing means is a threaded tube (or hollow screw) which screws into a complimentary threaded opening in the collar and engaging the hole in the shaft forming a tight seal such that the lumen of the tube and the lumen of the shaft are in fluid communication. This unique design allows the threaded tube to simultaneously serve as the affixing means for the collar and the flush port or the lumen of the shaft. The threaded design allows for easy removal of the tube or to change to a tube with different flush source connectors or to replace a damaged tube.

It is contemplated by the present invention that the apparatus described herein is suitable for attaching to any endoscopic surgical instruments including, but not limited to, laparoscopic or arthroscopic instruments and the like. The surgical tool can be any tool routinely used in endoscopic surgery, including, for example, tissue forceps, hemostats, retractors, clamps, scissors, needle holders and drivers, cautery tools, and the like. In general, any tool which is attached to a hollow elongate shaft is within the scope of the present invention. The apparatus can be constructed from any suitable materials including plastics, and metals. Examples of metals include, but are not limited to, aluminum, titanium and stainless steel. Examples of suitable plastics include acetal, polycarbonate, ABS, and the like.

BRIEF DESCRIPTION OF THE DRAWINGS

FIG. 1 is a perspective view of an embodiment of the present invention.

FIG. 2 is an exploded view of the apparatus of FIG. 1.

FIG. 3 is an end-on section view of the apparatus of FIG. 1 taken along lines 3—3.

DETAILED DESCRIPTION OF THE INVENTION

The present invention may be understood more readily by reference to the following detailed description of specific embodiments and the Figures included therein wherein like numbers represent like parts among the figures.

Referring now to FIG. 1, one embodiment of the removal collar assembly 10 is shown affixed to the shaft 12 of an endoscopic surgical instrument 11. The instrument 11 is of the type generally having a hollow elongated shaft 12 having a proximal-end 14, an opposite distal end 16, an external surface 18 and a luminal surface 20 defining a lumen 22; a surgical tool 23 having at least one articulated member 25 connected to the distal end 16 of the shaft 12; a handle 27, including actuating means 31, connected to the proximal end 14 of the shaft 12 for imparting motion to the articulated member 25; and an actuating rod 29 slidably disposed within the lumen 22 of the shaft 12 and connecting the actuating means of the handle 27 to the surgical tool 23, the shaft 12 further having a hole 26 in the external surface 18 in communication with the luminal surface 20.

FIG. 2 is an exploded view of the removable collar assembly 10 comprising a removable collar 28 on the shaft 12 and having an opening 30 therethrough which is in registration with the hole in the shaft 26; and an affixing means 32 for attaching the collar 28 to the shaft 12 dimensioned to be receivable within and detachably removable from the opening 30 in the collar 28 and the hole 26 in the shaft 12.

The collar assembly contemplated by the present invention can be affixed to endoscopic surgical instruments which have fixed shafts or to shafts which are rotatable about their longitudinal axis relative to the handle. In the embodiment depicted in FIG. 2, the shaft 12 is rotatably connected to the handle 11 by means of a set screw 24 which engages a journal 13 on the exterior surface 18 of the shaft 12, and the collar 28 also serves as the means for causing rotation of the shaft 12 and the surgical tool 23 about the longitudinal axis of the shaft 12 relative to the handle 11. The collar 28 can further comprise any of a number of configurations to provide the surgeon with a gripping means for ease in rotation the shaft 12. The embodiment depicted in the figures shows a plurality of alternating hand grip ribs 34 and detents 36 on the external surface 38 of the collar 28 which serve as the gripping means.

The apparatus of the present invention is designed such that the collar 28 can be removed from the shaft 11 for cleaning, or repair, or to change to a collar of a different configuration. It is contemplated by the present invention that the affixing means 31 for attaching the collar 28 to the shaft 11 can comprise one of any number of designs including but not limited to screws, dowel pegs or bayonet type connectors.

The affixing means 32 may further have an opening through its body which is in fluid communication with the lumen 22 of the shaft 12. The affixing means can therefore serve a dual function by providing a way to removably attach the collar 28 to the shaft 12 and also providing a means for flushing the lumen 22 of the shaft 12.

In the embodiment, shown last in FIG. 2 and FIG. 3, the affixing means 32 comprises a tube 40 having a first end 42, an opposite second end 44, a luminal surface 46 defining a lumen 48 and an opposite external surface such that the lumen 48 of the tube 40 is in fluid communication with the lumen 22 of the shaft 12. A portion of the surface of the opening in the collar 28 is threaded 54, and a portion of the external surface 50 of the tube 40 is threaded 56 complimentary to the threads 54 in the collar 28, the tube 40 being capable of removably being screwed into the opening in the collar 28 such that the first end 42 of the tube 40 forms a fluid tight seal with the hole 30 in the shaft 12. The tube 40 can further comprise a means for removing the tube 40 from the shaft 12 and collar 28. Wrench flats 58 are located on a portion of the external surface 50 of the tube 40 such that the affixing means 32 can be removed from the collar 18 by unscrewing the tube 40 from the collar 28.

The lumen 48 of the tube 40 can be sealed by means of a dust cover 60 or cap of another configuration. Alternatively, the affixing means 32 can comprise a set of interchangeable screws such that a solid screw (not shown) is utilized to seal the tube 40 thereby sealing the opening 26 in the shaft 12 during surgery and a complimentary hollow screw (the tube 40 as shown in FIG. 3) can be interchanged after surgery for flushing and cleaning the lumen 22 of the shaft 12.

The affixing means 32 of the apparatus 10 of the present invention can further provide a way to seat the tube 40 into a sealing and self-aligning engagement with the hole 26 in the shaft 12. It is contemplated by the present invention that any of a number of configurations between the first end 42 of the tube 40 and the hole 26 in the shaft 12 can be utilized to achieve a self-aligning and sealing engagement of the lumen 48 of the tube 40 and the hole 26 in the shaft 12 including, but not limited to, O ring seals, dog points, counter bores, and the like. In general, the hole 26 in the shaft 12 further comprises a first shape 62 and the first end 42 of the tube 40 comprises a second shape 64, complimentary to the first shape 62, whereby the first end 42 of the tube 40 is capable of seating within the hole 26 in the shaft 12 in sealing engagement with the shaft.

In the presently preferred embodiment depicted in FIG. 2 and FIG. 3, the first shape 64 is a circular champhered female countersink and the second shape 62 is a complimentary male chamfer such that the first end 42 of the tube 40 is capable of seating with the hole 26 in the shaft 12 in a self-aligning and sealing engagement.

As shown in FIG. 2 and FIG. 3, the apparatus also provides a means for attaching a flushing source (not shown) to the second end 44 of the tube 40. In the presently preferred embodiment, the attaching means is a luer lock thread 66.

The removable collar assembly 10 and affixing means 32 of the present invention provide an instrument with improved ease of assembly. In the presently preferred embodiments shown in the Figures, the removable collar assembly 10 is attached to the shaft 12 by simply aligning the opening 30 in the collar 28 with the hole 26 in the shaft 12 and screwing the affixing means into the opening 30 in the collar 28, such that the affixing means forms a sealing and self-aligning engagement with the hole 26 in the shaft 12. Assembly of the collar 28 to the shaft 12 is therefore accomplished without the use of solvent welds, soldering or brazing welds, adhesives, epoxy, and such. Likewise, because there are no permanent adhesives or welds, the collar 28 and affixing means 32 are easily removable for service, repair and replacement of damaged components by simply unscrewing the affixing means 32 from the collar 28.

One skilled in the art can appreciate that there are other designs which can be utilized to combine features of removability with simultaneous affixing and flushing means which are included within the scope of the present invention. For example, the tube 40 can be a conically tapered dowel which affixes the collar by removably wedging itself into position in the hole in the shaft such that fluid communication between the lumen of the tube and the lumen of the shaft is established.

Although the present invention has been described with reference to specific details of certain embodiments thereof, it is not intended that such details should be regarded as limitations upon the scope of the invention except as and to the extent that they are included in the accompanying claims.

What is claimed is:

1. An endoscopic surgical instrument comprising:

a) a hollow elongated shaft having a proximal end, an opposite distal end, an external surface, a luminal surface defining a lumen, and a hole in the external surface in communication with the luminal surface;

b) a surgical tool having at least one articulated member connected to the distal end of said shaft;

c) a handle, including actuating means, connected to the proximal end of said shaft for imparting motion to said articulated member;

d) an actuating rod slidably disposed within the lumen of said shaft and connecting said actuating means to said surgical tool;

e) a removable collar on the shaft and having an opening therethrough which is in registration with the hole in said shaft; and f) an affixing means for attaching said collar to said shaft dimensioned to be receivable within and detachably removable from the opening in said collar and the hole in said shaft, said affixing means having an opening therethrough which is in fluid communication with the lumen of said shaft.

2. The instrument of claim 1, wherein said shaft is rotatably connected to said handle and wherein said collar further comprises a means for causing rotation of said shaft and said surgical tool about the longitudinal axis of said shaft relative to said handle.

3. The instrument of claim 2, wherein said means for causing rotation of said shaft comprises at least one gripping means on the external surface of said collar.

4. The instrument of claim 1, wherein said affixing means comprises a tube having a first end, an opposite second end, a luminal surface defining said opening through said affixing means and an opposite external surface.

5. The instrument of claim 4, wherein at least a portion of the surface of the opening in said collar is threaded, and wherein at least a portion of the external surface of said tube is threaded complimentary to said collar, said tube being capable of removably being screwed into the opening in said collar such that the first end of said tube forms a fluid tight seal with the hole in said shaft.

6. The instrument of claim 4, wherein the hole in said shaft further comprises a first shape and the first end of said tube further comprises a second shape, complimentary to the first shape, whereby the first end of said tube is capable of seating within the hole in said shaft in sealing engagement with said shaft.

7. The instrument of claim 6, wherein the first shape is a circular champhered female countersink and the second shape is a complimentary male chamfer such that the first end of said tube is capable of seating with the hole in said shaft in a self-aligning and sealing engagement.

8. The instrument of claim 4, and further comprising a means for attaching a flushing source to the second end of said tube.

9. The instrument of claim 8, wherein the attaching means is a luer lock thread.

* * * * *